US 8,494,780 B2

(12) United States Patent
Tammero et al.

(10) Patent No.: US 8,494,780 B2
(45) Date of Patent: Jul. 23, 2013

(54) DATA TRANSFORMATION METHODS FOR MULTIPLEXED ASSAYS

(75) Inventors: Lance F. Bentley Tammero, Oakland, CA (US); John M. Dzenitis, Danville, CA (US); Benjamin J. Hindson, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 516 days.

(21) Appl. No.: 12/698,785

(22) Filed: Feb. 2, 2010

(65) Prior Publication Data
US 2011/0022344 A1  Jan. 27, 2011

Related U.S. Application Data

(60) Provisional application No. 61/228,499, filed on Jul. 24, 2009.

(51) Int. Cl.
| | | |
|---|---|---|
| *G06F 19/24* | (2011.01) | |
| *G06F 19/20* | (2011.01) | |
| *C12Q 1/68* | (2006.01) | |
| *G01N 33/53* | (2006.01) | |
| *G01N 33/569* | (2006.01) | |

(52) U.S. Cl.
CPC ............ *G06F 19/24* (2013.01); *G06F 19/20* (2013.01); *C12Q 1/6813* (2013.01); *G01N 33/53* (2013.01); *G01N 33/569* (2013.01); *C12Q 1/6888* (2013.01)
USPC .............................. 702/19; 435/6.1; 435/7.1

(58) Field of Classification Search
None
See application file for complete search history.

(56) References Cited

U.S. PATENT DOCUMENTS
5,624,802 A * 4/1997 Urdea et al. ............... 435/6.11

OTHER PUBLICATIONS

Lenhoff, R. J. et al. Multiplexed molecular assay for rapid exclusion of foot-and-mouth disease. Journal of Virological Methods 153, 61-69 (2008).*
Thompson, D.; Muriel, P.; Russell, D.; Osborne, P.; Bromley, A.; Rowland, M.; Creigh-Tyte, S.; Brown, C. Rev. Sci. Tech. Off. Int. Epiz. 2002, 21, 675-687.
Bourn, J. Department for environment, food and rural affairs, National Audit Office, U.K., 2005, pp. 1-61.
Kitching, R. P.; Hutber, A. M.; Thrusfield, M. V. Veterinary Journal 2005, 169, 197-209.
Reid, S. M.; Panda, S.; King, D. P.; Hutchings, G. H.; Shaw, A. E.; Ferris, N. P.; Zhang, Z. D.; Hillerton, J. E.; Paton, D. J. Vet. Res. 2006, 37, 121-132.
Zhang, Z. D.; Alexandersen, S. J. Virol. Methods 2003, 111, 95-100.
Callahan, J. D.; Brown, F.; Csorio, F. A.; Sur, J. H.; Kramer, E.; Long, G. W.; Lubroth, J.; Ellis, S. J.; Shoulars, K. S.; Gaffney, K. L.; Rock, D. L.; Nelson, W. M. J. Am. Vet. Med. Assoc. 2002, 220, 1636-1642.
Reid, S. M.; Ferris, N. P.; Hutchings, G. H.; Zhang, Z. D.; Belsham, G. J.; Alexandersen, S. J. Virol. Methods 2002, 105, 67-80.
Oleksiewicz, M. B.; Donaldson, A. I.; Alexandersen, S. J. Virol. Methods 2001, 92, 23-35.
Letellier, C.; Kerkhofs, P. J. Virol. Methods 2003, 114, 21-27.

(Continued)

*Primary Examiner* — Soren Harward
(74) *Attorney, Agent, or Firm* — Steinfl & Bruno, LLP

(57) ABSTRACT

Methods to improve the performance of an array assay are described. A correlation between fluorescence intensity-related parameters and negative control values of the assay is determined. The parameters are then adjusted as a function of the correlation. As a result, sensitivity of the assay is improved without changes in its specificity.

8 Claims, 4 Drawing Sheets

OTHER PUBLICATIONS

Bhudevi, B.; Weinstock, D. Vet. Microbiol. 2001, 83, 1-10.

Baxi, M.; McRae, D.; Baxi, S.; Greiser-Wilke, I.; Vilcek, S.; Amoako, K.; Deregt, D. Vet. Microbiol. 2006, 116, 37-44.

Johnson, D. J.; Wilson, W. C.; Paul, P. S. Vet. Microbiol. 2000, 76, 105-115.

Jimenez-Clavero, M. A.; Aguero, M.; Miguel, E. S.; Mayoral, T.; Lopez, M. C.; Ruano, M. J.; Romero, E.; Monaco, F.; Polci, A.; Savini, G.; Gomez-Tejedor, C. J. Vet. Diagn Invest. 2006, 18, 7-17.

Nitsche, A.; Buttner, M.; Wilhelm, S.; Pauli, G.; Meyer, H. Clin. Chem. 2006, 52, 316-319.

Wilson, W. J.; Erler, A. M.; Nasarabadi, S. L.; Skowronski, E. W.; Imbro, P. M. Mol. Cell. Probes 2005, 19, 137-144.

Dunbar, S. A. Clin. Chim. Acta 2006, 363, 71-82.

Yan, X. M.; Zhong, W. W.; Tang, A. J.; Schielke, E. G.; Hang, W.; Nolan, J. P. Anal. Chem. 2005, 77, 7673-7678.

Hindson, B. J.; McBride, M. T.; Makarewicz, A. J.; Henderer, B. D.; Setlur, U. S.; Smith, S. M.; Gutierrez, D. M.; Metz, T. R.; Nasarabadi, S. L.; Venkateswaran, K. S.; Farrow, S. W.; Colston, B. W.; Dzenitis, J. M. Anal. Chem. 2005, 77, 284-289.

Perkins, J.; Clavijo, A.; Hindson, B. J.; Lenhoff, R. J.; McBride, M. T. Anal. Chem. 2006, 78, 5462-5468.

Fitch, J. P. Evolutionary Theories of Detection. DHS IEEE Conference, Boston MA, Apr. 25-28, 2005. UCRL CONF-212194. http://www.llnl.gov/tid/lof/documents/pdf/319757.pdf.

Zweig, M. H.; Campbell, G. Clin. Chem. 1993, 39, 561-577.

Greiner, M.; Pfeiffer, D.; Smith, R. D. Prev. Vet. Med. 2000, 45, 23-41.

Greiner, M.; Sohr, D.; Gobel, P. J. Immunol. Methods 1995, 185, 123-132.

Dunbar, S.A., Vander Zee, C.K., Oliver, K.G., Karem, K.L., Jacobson, J.W., 2003. Quantitative, multiplexed detection of bacterial pathogens: DNA and protein applications of the Luminex LabMAP system. Journal of Microbiological Methods 53, 245-252.

Finney, D.J., 1978. Statistical Methods in Biological Assays, 3rd ed. MacMillan Publishing Co., Inc., New York, NY, pp. 394-398 (Assays based on quantal responses).

Flint, S.J., Enquist, L.W., Racaniello, V.R., Skalka, A.M., 2004. Principles of Virology Molecular Biology, Pathogenesis, and Control of Animal Viruses, 2nd ed. ASM Press, Washington, DC, p. 35.

Haydon, D.T., Bastos, A.D.S., Awadalla, P., 2004. Low linkage disequilibrium indicative of recombination in foot-and-mouth disease virus gene sequence alignments. Journal of General Virology 85, 1095-1100.

Hietala, S., Crossley, B., 2006. Armored RNA as virus surrogate in a real-time reverse transcriptase PCR assay proficiency panel. Journal of Clinical Microbiology 44, 67-70.

Kellar, K.L., Iannone, M.A., 2002. Multiplexed microsphere-based flow cytometric assays. Experimental Hematology 30, 1227-1237.

McBride, M.T., Gammon, S., Pitesky, M., O'Brien, T.W., Smith, T., Aldrich, J., Langlois, R., Venkateswaran, K.S., 2003. Multiplexed liquid arrays for simultaneous detection of simulants of biological-warfare agents. Analytical Chemistry 75, 1924-1930.

Reed, L.J., Muench, L.H., 1938. A simple method of estimating fifty percent endpoints. American Journal of Hygiene 27, 493-497.

Reid, S.M., King, D.P., Shaw, A.E., Knowles, N.J., Hutchings, G.H., et al., 2006. Development of a real-time reverse transcription polymerase chain reaction assay for detection of marine caliciviruses (genus *Vesivirus*). Journal of Virological Methods 140, 166-173.

Ripa, T., Nilsson, P.A., 2007. A *Chlamydia trachomatis* strain with a 377-bp deletion in the cryptic plasmid causing false-negative nucleic acid amplification tests. Sexually Transmitted Diseases 35, 255-256.

Rweyemamu, M.M., Astudillo, V.M., 2002. Foot and mouth disease: facing the new dilemmas. Revue Scientifique et Technique de l Office International des Epizooties 21, 765-773.

Scudamore, J.M., Trevelyan, G.M., Tas, M.V., Varley, E.M., Hickman, G.A., 2002. Carcass disposal: lessons from Great Britain following the foot and mouth disease outbreaks of 2001. Revue Scientifique et Technique 21, 775-787.

Slezak, T., Kuczmarski, T., Ott, L., Torres, C., Medeiros, D., et al., 2003. Comparative genomics tools applied to bioterrorism defense. Brief Bioinformatics 4, 133-149.

Non-Final Office Action issued for U.S. Appl. 12/607,956, filed Oct. 28, 2009 in the name of Lance F. Bentley Tammero, mail date: Jan. 24, 2012.

Hindson, B.J. et al. Diagnostic Evaluation of Multiplexed Reverse Transcription-PCR Microsphere Array for Detection of Foot-and-Mouth and Look-Alike Disease Viruses, Journal of Clinical Microbiology, Mar. 2008, vol. 46, No. 3, pp. 1081-1089.

Restriction Requirement for U.S. Appl. 12/607,956, filed Oct. 28, 2009 in the name of Lance F. Bentley Tammero, mail date: Dec. 5, 2011.

* cited by examiner

DATA TRANSFORMATION METHODS FOR MULTIPLEXED ASSAYS

CROSS REFERENCE TO RELATED APPLICATIONS

The present application claims priority to U.S. Prov. App. No. 61/228,499 filed on Jul. 24, 2009 and incorporated herein by reference in its entirety. The present application is also related to U.S. application Ser. No. 12/607,956 filed on Oct. 28, 2009 for "Methods for Threshold Determination in Multiplexed Assays", also incorporated herein by reference in its entirety.

STATEMENT OF GOVERNMENT GRANT

The United States Government has rights in this invention pursuant to Contract No. DE-AC52-07NA27344 between the United States Department of Energy and Lawrence Livermore National Security, LLC for the operation of Lawrence Livermore National Laboratory.

FIELD

The present disclosure relates to assays. In particular, the present disclosure relates to data transformation methods to improve performance of multiplexed liquid array assays.

BACKGROUND

An effective assay reacts to positive samples with a range of responses distinct and separate from the responses resulting from negative samples. Variation in response measurements causes greater spread in the distributions of responses to both positive and negative samples, increasing the likelihood that these distributions will overlap. Increased overlap in the response to positive and negative signals degrades assay performance resulting in reduced sensitivity and specificity.

In multiplexed arrays such as the multiplexed PCR liquid array assay, there are many possible sources of variation. Variability in the efficiency of the nucleic acid extraction, the extent of PCR amplification, and hybridization of amplified product to the probe-microsphere conjugates affect the median fluorescent intensity (MFI) measurements [see reference 15]. Non-specific interactions between the primers and variability in the binding of the fluorophore to the probes results can result in disparity in the responses to negative samples. The composition of the sample matrix (e.g., blood, serum, saliva etc) may also affect the measurement responses for both positive and negative samples as well. In addition to these effects, which can be seen in measurements made by a single laboratory or operator, there are sources of variation owing to differences between laboratories, such as differences in thermal cycler ramp times, ambient temperatures, and the manual techniques used by various operators.

Therefore, a problem with current techniques is that responses generated during a multiplexed assay such as a PCR diagnostic assay using liquid array detection are subject to multiple sources of variation. Variation in the median fluorescent intensity (MFI) responses results in elevated threshold values and thus reduced true positive rates.

SUMMARY

According to a first aspect, a method for improving performance of an assay comprising a plurality of signatures is provided, comprising, for each signature: determining fluorescence intensity measurements generated by negative samples of a target; determining negative control fluorescence intensity measurements related to the fluorescence intensity measurements generated by the negative samples; determining a correlation between the fluorescence intensity measurements and the negative control fluorescence intensity measurements; and adjusting the fluorescence intensity measurements as a function of the correlation and the negative control values.

According to a second aspect, a method of obtaining a transformed assay response distribution from an assay used to detect a target is provided, comprising: determining an assay response distribution for a plurality of signatures on a negative sample, thus obtaining a signature negative response distribution; for each signature, providing an indicator by determining a correlation variance measure between a signature measurement and a signature negative control measurement; and for each signature, transforming the signature negative response distribution as a function of the signature negative control measurement, thus providing a transformed assay response distribution.

Further aspects of the disclosure are provided in the specification, drawings and claims of the present application.

BRIEF DESCRIPTION OF THE DRAWINGS

The accompanying drawings, which are incorporated into and constitute a part of this specification, illustrate one or more embodiments of the present disclosure and, together with the detailed description and the examples, serve to explain the principles and implementations of the disclosure.

DESCRIPTION OF EXAMPLE EMBODIMENTS

Figure 1:
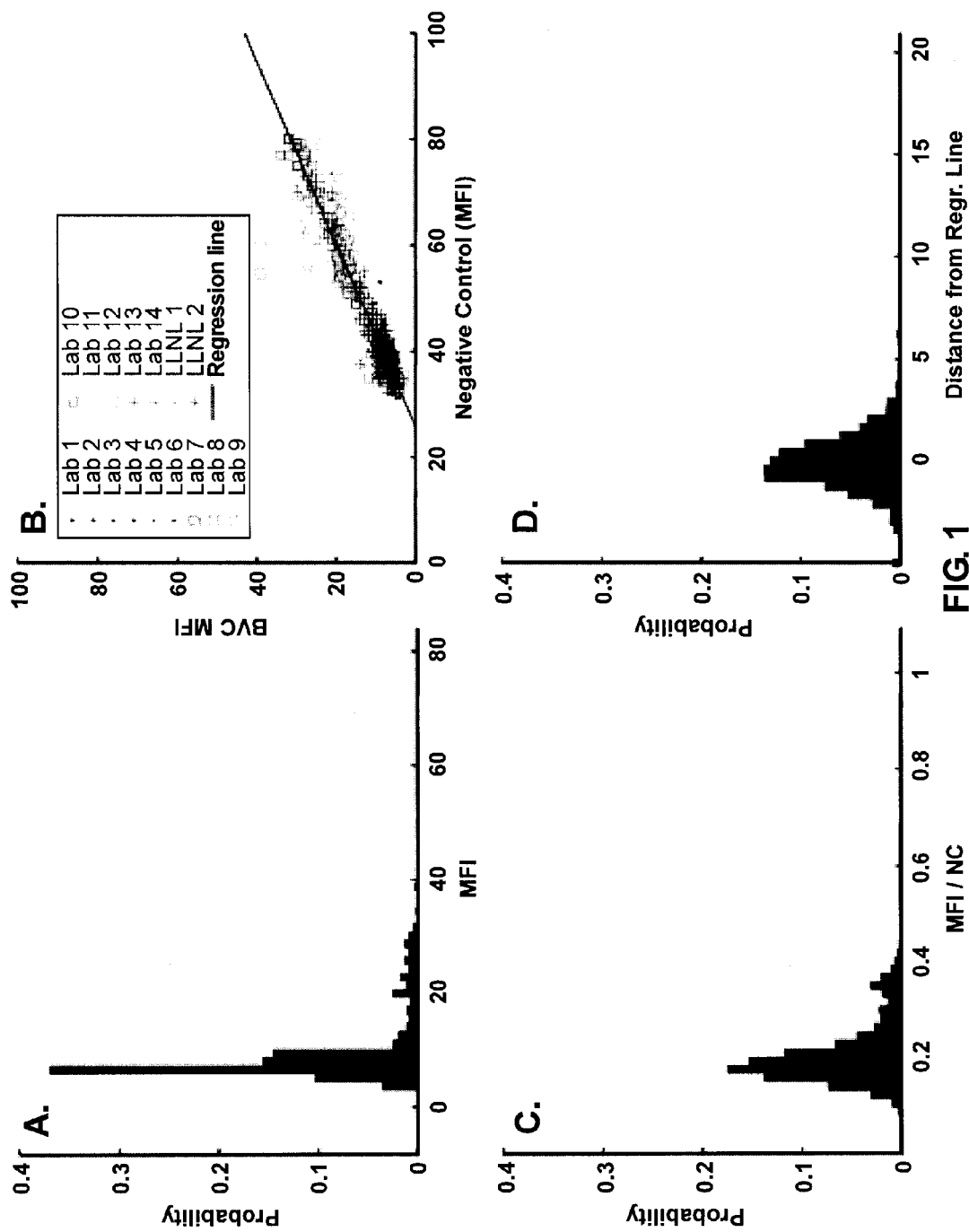
FIG. 1A shows the probability density function (PDF) of untransformed median fluorescence intensity (MFI) responses of a bovine viral diarrhoea (BVD) signature to negative samples, with a sharp peak followed by an extended tail.
FIG. 1B shows negative control (NC) MFI measurements from which the tail of FIG. 1A results, indicating a correlation between the response as measured by the BVD signature and the negative control.
FIG. 1C shows a first embodiment of the present disclosure where a transformation is obtained by scaling by the negative control.
FIG. 1D shows a second embodiment of the present disclosure where a transformation is obtained by taking a distance from a regression line

The term "assay" as used herein indicates a procedure for detecting a target in an organism or organic sample. The term "detect" or "detection" as used herein indicates the determination the existence, presence or fact of a target or signal in a limited portion of space, including but not limited to a sample, a reaction mixture, a molecular complex and a substrate. Bioassays and immunoassays are among the many varieties of assays directed to detection of targets of biological and/or chemical interest. Additional exemplary assays detect targets related to such processes as enzyme activity, antigen capture, stem cell activity, and competitive protein binding.

Detection of targets can be typically performed by using "signatures" i.e. capture agents comprising an oligonucleotide sequence designed to bind a desired target used in combination with suitable labels and/or labeled molecule. The term "capture agent" or "captor" as used herein indicates a compound that is able to specifically bind a target wherein the terms "specific" "specifically" or specificity" as used herein with reference to the binding of a molecule to another refers to the recognition, contact and formation of a stable complex between the molecule and the another, together with substantially less to no recognition, contact and formation of a stable complex between each of the molecule and the another with other molecules. Exemplary specific bindings are antibody-antigen interaction, cellular receptor-ligand interactions, polynucleotide hybridization, enzyme substrate interactions etc.

The terms "label" and "labeled molecule" as used herein as a component of a complex or molecule refer to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like.

The term "fluorophore" refers to a substance or a portion thereof which is capable of exhibiting fluorescence in a detectable image.

As a consequence the wording "labeling signal" as used herein indicates the signal emitted from the label that allows detection of the label, including but not limited to radioactivity, fluorescence, chemolumiescence, production of a compound in outcome of an enzymatic reaction and the likes. Exemplary signatures are provided by two primers and a probe that specifically bind a specific genetic sequence. Other examples might include labeling via the bonding between antigen and antibodies.

The term "target" as used herein indicates an analyte of interest. The term "analyte" refers to a substance, compound or component whose presence or absence in a sample has to be detected. Analytes include but are not limited to biomolecules and in particular biomarkers. The term "biomolecule" as used herein indicates a substance compound or component associated to a biological environment including but not limited to sugars, aminoacids, peptides proteins, oligonucleotides, polynucleotides, polypeptides, organic molecules, haptens, epitopes, biological cells, parts of biological cells, vitamins, hormones and the like. The term "biomarker" indicates a biomolecule that is associated with a specific state of a biological environment including but not limited to a phase of cellular cycle, health and disease state. The presence, absence, reduction, upregulation of the biomarker is associated with and is indicative of a particular state.

The term "sample" as used herein indicates a limited quantity of something that is indicative of a larger quantity of that something, including but not limited to fluids from a biological environment, specimen, cultures, tissues, commercial recombinant proteins, synthetic compounds or portions thereof.

The applicants have noted that the control values generated by the assays do not affect the analyses, with the exception of ruling our likely invalid data. In particular, additional information present in the control readings may be extracted and used to transform the data to improve its representation of the presence or absence of virus.

The methods herein described are further illustrated in the following examples, which are provided by way of illustration and are not intended to be limiting. In particular, in the following examples, target detection is exemplified in experiments directed to identify Foot and Mouth Disease (FMD). FMD is a highly contagious viral disease of cloven-hoofed animals. Although the US has been free of FMD since 1929, the disease is endemic to parts of the Middle East, Africa, Asia and South America. An FMD outbreak in the U.S. has the potential to severely impact the economy. The 2001 FMD outbreak in the UK cost the tax payer more than US$5 billion [see references 1-3].

Early detection is critical for reducing both the spread of disease and the economic impact of FMD. However, symptomatic diagnosis is confounded by other vesicular diseases, termed "look-alikes", some of which are endemic to regions of the US. At present, a farmer, producer or veterinarian suspicious of FMD, based on their clinical observations, could request a State or Federal veterinarian to collect and submit a sample (usually vesicular fluid, tissue or blood) to the Plum Island Animal Disease Center for testing.

Diagnosis of the index case requires confirmatory laboratory testing using techniques such as virus isolation, antigen ELISA, polymerase chain reaction (PCR), and sequencing, which can take at least several days to complete. In the event of positive confirmation of FMD, the Federal government may authorize foot-and-mouth disease virus (FMDV) testing at regional veterinary diagnostic laboratories. For samples confirmed negative for FMD, State or Regional laboratories typically conduct an investigation for FMD look-alike diseases.

Molecular diagnostics, primarily real-time reverse transcriptase polymerase chain reaction (RT-PCR) assays, enable rapid detection of FMDV [see references 4-8], as well as FMDV look-alikes including bovine viral diarrhea virus (BVDV) [see references 9-11], bluetongue virus [see references 12 and 13] and parapoxviruses [see reference 14]. Multiplexing of real-time RT-PCR assays is limited by the broad emission spectra of the fluorescent probes and commercial instruments typically offer four discrete optical channels or less. Testing for FMD and look-alike diseases using conventional real-time PCR requires each disease-specific assay to be run individually. Demand for instrumentation and reagents can often exceed laboratory capacity. Combining individual assays into a single multiplexed diagnostic test that simultaneously differentiates FMD from look-alike diseases could provide a means of rapid, cost-effective viral identification for suspect samples, and could enable early detection if used for routine or targeted surveillance.

In accordance with the present disclosure, methods are provided to transform the measured MFI values from an individual assay (e.g., a micro array based multiplexed assay) using the information present in the negative controls for the same measurement in order to remove a source of variation in the background signal.

The term "median fluorescence intensity" or "MFI" as used herein indicates the density of specific molecules on the surface of a microsphere. It is a value reflecting the level of fluorescence of a population of microspheres labeled with an identical reagent (references 16-18). The person skilled in the art will understand, upon reading of the present disclosure, that other statistical parameters related to fluorescence intensity can be used, such as the mean (or average) fluorescent intensity.

Negative control values are derived from samples lacking the target of interest and are used as a control. The thresholds resulting from this "cleaner" background signal will improve the sensitivity of the assay (proportion of true positives) without any change in the assay's false positive rate. As a consequence, assay specificity (proportion of true negatives) will remain unchanged. The term "threshold" as used herein indicates a value above which a response is ruled positive. An example of a threshold would be a specific MFI value that needs to be exceeded for an assay to be ruled positive.

According to embodiments of the present disclosure, fluorescence intensity-related (e.g., MFI) values generated by blank (negative) samples were used. Based on these values, two methods can be used to transform the measured MFI values.

According to a first embodiment, the MFI response for each individual signature (untransformed MFI measurement) is divided by the negative control (NC) MFI value, thus obtaining transformed MFI measurements through scaling normalization via negative control.

According to a second embodiment, the linear model best describing the relationship between the negative control MFI value and the MFI value for each signature (untransformed MFI measurement) is determined. Such relationship can be determined, for example, by reduced major axis linear regression. The residual distances from each individual point to the regression line along the vector orthogonal to the regression line can be calculated, thus providing transformed MFI measurements through computation of such distance.

In both embodiments above, thresholds for the transformed MFI measurements can be calculated such that, for example, the probability of a Type I error ($\alpha$) was held at 0.05.

The transformed MFI measurements obtained through one of the two embodiments described above can be compared to previously determined threshold values to determine the rate at which the measured exceed threshold, i.e. the true positive (TP) rate. Once this is done, the TP rates for transformed and untransformed measurements can be compared. Transformations and data processing can be carried out using, for example, using a customizable programming environment capable of performing scientific calculations, such as Matlab®, Microsoft Excel®, or Python®.

Because threshold values are determined, as mentioned above, by the MFI responses to negative samples, variation in these MFI responses impacts assay performance. The variation in the MFI response to negative samples is characterized via probability density functions (PDFs). An increase in the spread of the PDF results in a larger threshold value, which may cause an increase in the limit of detection as shown, for example, in U.S. patent application Ser. No. 12/607,956 for "Methods for Threshold Determination in Multiplexed Assays", filed on Oct. 28, 2009, and incorporated herein by reference in its entirety.

As shown in FIG. 1A, in an exemplary case of a BVD signature's response to negative samples, the most frequently occurring MFI value and the median MFI value are both 7. However, the threshold value exceeds by 0.5% of the negative samples is 34. Therefore, variation in the MFI response to negative examples extends the tail of the distribution, moving the threshold value (in this case 34) further away from the MFI values (in this case 7) that occur most frequently. As a consequence, responses to small concentrations of virus may have MFI values similar to those that make up the extended tail of FIG. 1A, resulting in undesired false negative rulings, thus reducing the sensitivity of the assay.

However, using the transformations of FIGS. 1C and 1D to account for variation in the raw data will enhance the difference between negative samples with higher MFI values and positive samples with lower MFI values, resulting in improvements in assay performance as measured by the rate at which positive samples are correctly identified, i.e. the true positive (TP) rate.

As also noted before, the responses provided by internal assay controls reflect the conditions under which the assay was run. For example, variation in MFI signal of the negative control (NC), a sequence not matching the published genomes of terrestrial organisms, may be indicative of the portion of the response due to non-specific binding or differences in operator technique. Variations in the MFI response for virus-sensitive signatures to negative samples may be caused by similar assay conditions, suggesting the likelihood of correlation between those MFI signals and the NC signal. Such a correlation is evident in the experiments performed by Applicants.

In particular, FIG. 1B illustrates the correlation between a signature sensitive to BVD and the negative control in response to negative samples ($r^2$=0.9). The diagram of FIG. 1B further illustrates how variation in the distribution of MFI measurements can be traced back to individual laboratories. For example, Lab 14 produced a number of measurements for which both the BVD and NC MFI signals were at the lower end of their ranges, while Labs 7 and LLNL 1 generated signals for which the BVD and NC MFI levels were elevated.

The $r^2$ values quantify the percentage of variance in each signature response that is reflected in negative control response. For instance, the $r^2$ value of 0.9 for the BVD-1a signature indicates that 90% of the variation of the in the MFI value of the BVD-1a signature is present in the variance in the negative control MFI. The $r^2$ values for 15 of the 17 signatures of the panel were also significant (>0.75), indicating a high level of correlation between the signature MFI values and the negative control value in response to negative samples.

In view of the above, Applicants have noted that a transformation designed to remove the variance evident in the negative control signal from the virus-sensitive signatures would enhance the distinction between elevated MFI signals generated by negative samples (which would simultaneously show an elevated NC signal) and elevated MFI signal from weakly positive samples (which would not show an elevated NC signal).

In accordance with several embodiments of the present disclosure, two transformations can be used to adjust for variation in MFI signals. In a first case (scaling transformation), shown in FIG. 1C, each MFI value is divided by the negative control (NC) value. In accordance with this normalization, samples for which NC MFI values are elevated are likely to result in higher signature MFI values. Instead of calculating a threshold with respect to the raw MFI signal, all signals and thresholds are now described as scalar multiples of the negative control value. In a second case (distance from regression line transformation), shown in FIG. 1D, the MFI value for each signature is replaced with the distance between each (NC, MFI) coordinate along the vector orthogonal to the regression line. After this manipulation, threshold levels are now taken with respect to distance from the regression line along the orthogonal vector.

The goal for both of these transformations is to enhance the difference between the MFI distributions resulting from the presence or absence of the virus. The PDF of negative sample MFI values for untransformed data (FIG. 1A) differ from Gaussian PDF because of the extended tail. Both the scaling transformation and the distance from regression line transformation reduce the tail of the distribution, as seen by comparing FIG. 1A with FIG. 1C or FIG. 1D. By reducing the tail of the distribution of MFI values for negative samples, the range of MFI values that can be generated by both positive and negative samples is reduced, which leads to improved assay performance.

Once the transformations of FIG. 1C or FIG. 1D have been performed, thresholds may be established in accordance to the teachings of U.S. Ser. No. 12/607,956 filed on Oct. 28, 2009, incorporated herein by reference in its entirety.

Figure 2:
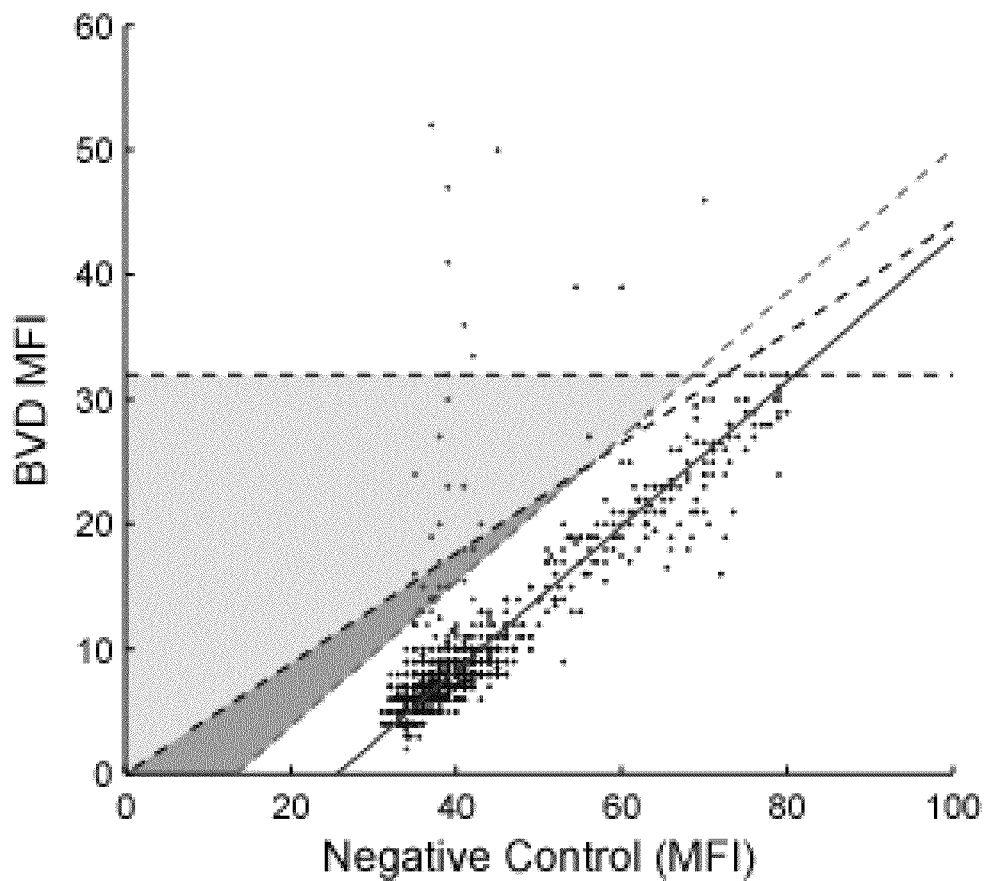
FIG. 2 shows the results of transformations of negative response distributions according to the present disclosure.

Data transformation better separates the responses of positive and negative samples. This can be seen by plotting the relationship between NC MFI and BVD MFI for samples run during an inter-laboratory comparison, as shown in FIG. 2.

The dashed lines indicate thresholds based upon untransformed data (horizontal), responses scaled by the negative control (NC) and distances measured from the regression line plotted with responses to negative and spiked BVD positive samples. In the example of the figure, all thresholds were chosen to yield a false positive rate of 0.005. The light gray region indicates MFI pairings that would result in a negative response for untransformed data, but would generate positive response after either transformation. The darker gray region indicates where the distance from regression line transformation only generates positive responses. The BVD MFI values generated by a number of responses to positive samples that were beyond the limit of the y-axis would generate positive responses independent of whether the data was transformed and thus were excluded to improve the readability of the figure.

Figure 3:
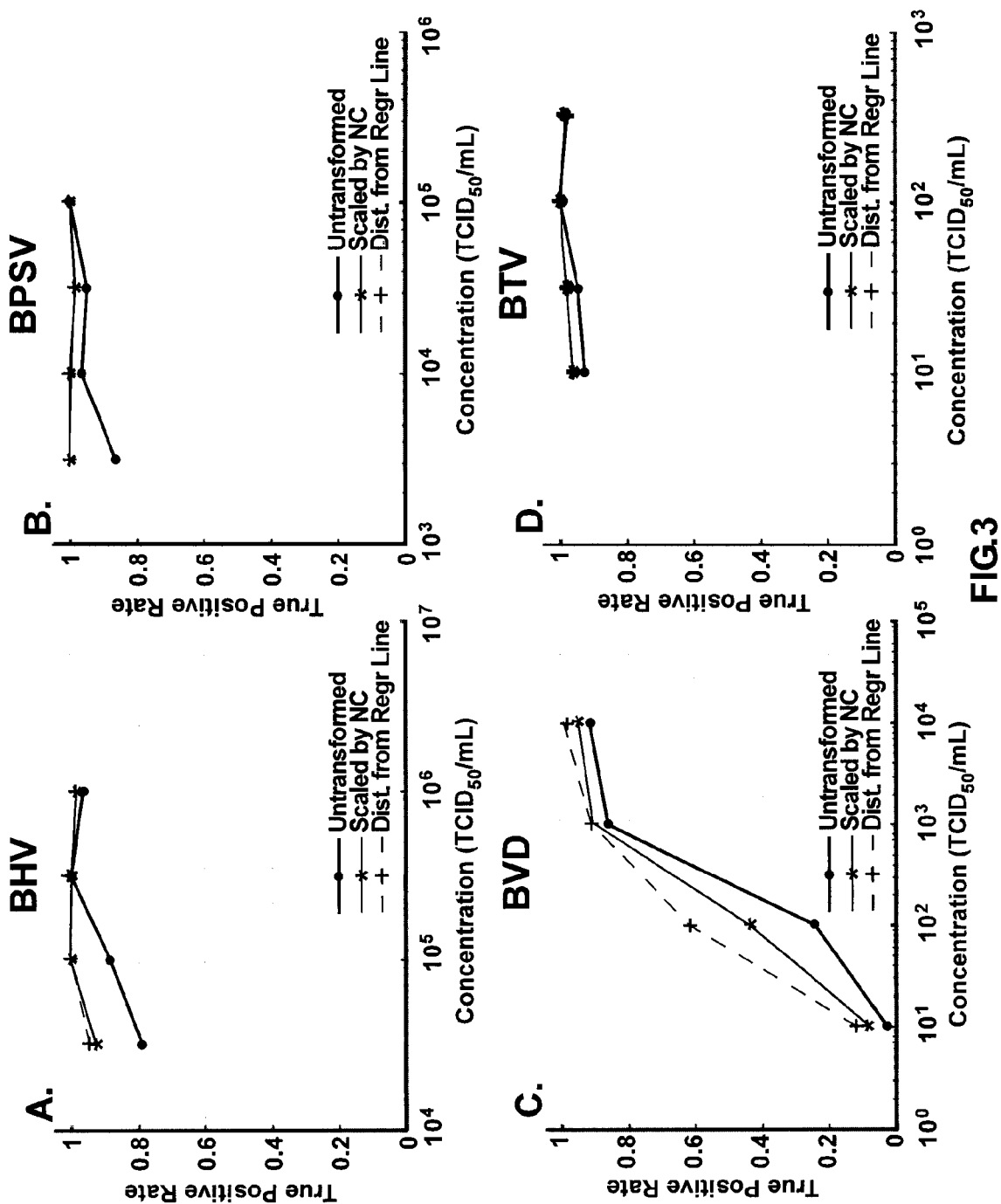
FIGS. 3A-3D show the results of transformations of negative response distributions according to the present disclosure. In particular, true positive (TP) rate per concentration of virus for four signatures (BHV, BPSV, BVD, BTV) is respectively indicated.

After transformation, the thresholds were set based upon a FP rate of 0.005. Samples generating NC MFI and BVD MFI value pairings within the light gray region, originally ruled negative, would be ruled positive after the scaling transformation or the distance from regression line transformation. Samples generating NC and MFI value pairings within the dark gray region would be ruled positive after the distance from regression line transformation, but not the scaling transformation. The BVD MFI values generated by a number of responses to positive samples that were beyond the limit of the y-axis would generate positive responses independent of whether the data was transformed and thus were excluded to improve the readability of FIG. 2. Thus, both transformation methods result in improved threshold values that better separate the distributions of positive and negative samples, and thus increase in the true positive (TP) rate, while the FP rate is held constant Applicants compared the TP rate curves as a function of virus concentration of virus for transformed and untransformed data, as shown in FIG. 3. The TP rate is increased for signature BHV-1 at the lower two concentrations, see FIG. 3A. At the higher two concentrations the TP rate for untransformed data is close to 1, thus there is little improvement as a result of transformation. Similarly, for the BPSV-1 signature, see FIG. 3B, TP rate increases after data transformation at the lowest BPSV concentration, while remaining unchanged for higher concentrations. The signature responsive to BVD showed increased TP rate after transformation for all concentrations (FIG. 3C) with transformation via distance from the regression line transformation, resulting in a larger increase in TP rate than transformation via scaling. The TP rate for the BTV-2 signature was close to 1.0 at all concentrations (FIG. 3D), thus data transformation had little impact on TP rate.

Figure 4:
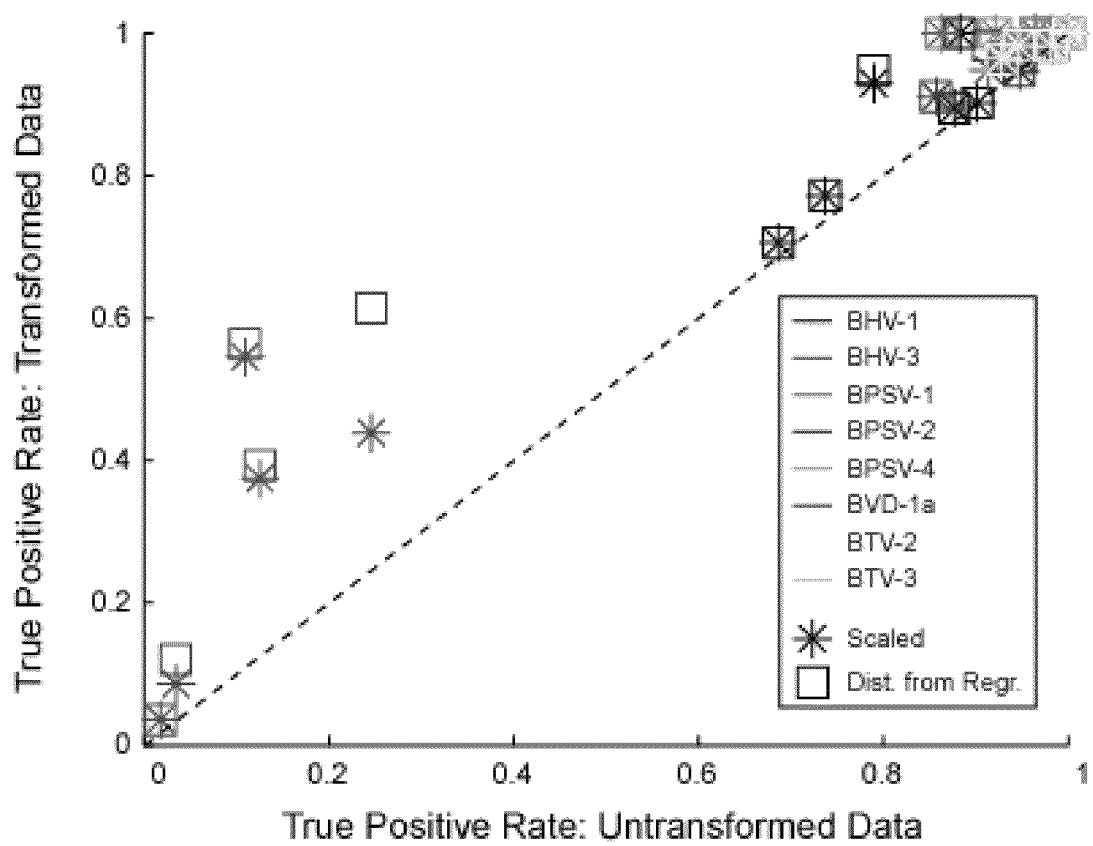
FIG. 4 shows a summary of improvement in true positive rate for all signatures tested by using the transformations of the present disclosure.

For multiple signatures, scaling or finding the distance to the regression line results in improvement in TP rate without cost in FP rate. This is particularly evident at lower concentrations of virus for which the MFI signals are weaker. FIG. 4 summarizes these findings by plotting the TP rate calculated using the transformed MFI values to that using the raw MFI values for each concentration of virus used in the inter-laboratory comparison (each point represents a single concentration). The dashed line of FIG. 4 (unity line) indicates identical true positive rates for the transformed and untransformed data. Points above the unity line indicate that improvement occurs with data transformation, points below the unity line indicate worse performance after transformation. FIG. 4 shows that all of the points lie either on or above the unity line, indicating that the TP rate is either improved or remains the same. At concentrations that generate high TP rates without data transformation, there is less room for improvement, resulting in the clustering around the upper right corner. The transformation of MFI data improves TP rate, while remaining computationally simple, indicating that improvements in TP rate can be made without altering assay reagents or cost per assay or affecting the FP rate of the assay.

Possible hardware components used to perform the teachings in accordance with the disclosure are those adopted to run a PCR-based biodetection assay that includes a negative control and some measure of chemiluminescence. The hardware components collect the data used in accordance with the disclosure. As for the software components used following the collection of the data, any commercially available package that is capable of reading in text data and performing several standard mathematical calculations can be used. By way of example, the methods of the present disclosure can performed by way of packages such as Matlab®, Microsoft Excel®, or through software code generated in a programming language like Java® or Python®.

The examples set forth above are provided to give those of ordinary skill in the art a complete disclosure and description of how to make and use the embodiments of the devices, systems and methods of the disclosure, and are not intended to limit the scope of what the inventors regard as their disclosure. All patents and publications mentioned in the disclosure are indicative of the levels of skill of those skilled in the art to which the disclosure pertains. All references cited in this disclosure are incorporated by reference to the same extent as if each reference had been incorporated by reference in its entirety individually.

The entire disclosure of each document cited (including patents, patent applications, journal articles, abstracts, laboratory manuals, books, or other disclosures) is hereby incorporated herein by reference.

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The terms "multiple" and "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications may be made without departing from the spirit and scope of the present disclosure. In particular, modifications of the above-described modes for carrying out the disclosure that are obvious to persons of skill in the art are intended to be within the scope of the present disclosure. Accordingly, other embodiments are within the scope of the following claims.

REFERENCES (1) Thompson, D.; Muriel, P.; Russell, D.; Osborne, P.; Bromley, A.; Rowland, M.; Creigh-Tyte, S.; Brown, C. *Rev. Sci. Tech. Off. Int. Epiz.* 2002, 21, 675-687.
(2) Bourn, J. Department for environment, food and rural affairs, National Audit Office, U.K., pp 1-61.
(3) Kitching, R. P.; Hutber, A. M.; Thrusfield, M. V. *Veterinary Journal* 2005, 169, 197-209.
(4) Reid, S. M.; Parida, S.; King, D. P.; Hutchings, G. H.; Shaw, A. E.; Ferris, N. P.; Zhang, Z. D.; Hillerton, J. E.; Paton, D. *J. Vet. Res.* 2006, 37, 121-132.
(5) Zhang, Z. D.; Alexandersen, S. *J. Virol. Methods* 2003, 111, 95-100.
(6) Callahan, J. D.; Brown, F.; Csorio, F. A.; Sur, J. H.; Kramer, E.; Long, G. W.; Lubroth, J.; Ellis, S. J.; Shoulars, K. S.; Gaffney, K. L.; Rock, D. L.; Nelson, W. M. *J. Am. Vet. Med. Assoc.* 2002, 220, 1636-1642.
(7) Reid, S. M.; Ferris, N. P.; Hutchings, G. H.; Zhang, Z. D.; Belsham, G. J.; Alexandersen, S. *J. Virol. Methods* 2002, 105, 67-80.
(8) Oleksiewicz, M. B.; Donaldson, A. I.; Alexandersen, S. *J. Virol. Methods* 2001, 92, 23-35.
(9) Letellier, C.; Kerkhofs, P. *J. Virol. Methods* 2003, 114, 21-27.
(10) Bhudevi, B.; Weinstock, D. *Vet. Microbiol.* 2001, 83, 1-10.
(11) Baxi, M.; McRae, D.; Baxi, S.; Greiser-Wilke, I.; Vilcek, S.; Amoako, K.; Deregt, D. *Vet. Microbiol.* 2006, 116, 37-44.
(12) Johnson, D. J.; Wilson, W. C.; Paul, P. S. *Vet. Microbiol.* 2000, 76, 105-115.
(13) Jimenez-Clayero, M. A.; Aguero, M.; Miguel, E. S.; Mayoral, T.; Lopez, M. C.; Ruano, M. J.; Romero, E.; Monaco, F.; Polci, A.; Savini, G.; Gomez-Tejedor, C. *J. Vet. Diagn Invest.* 2006, 18, 7-17.
(14) Nitsche, A.; Buttner, M.; Wilhelm, S.; Pauli, G.; Meyer, H. *Clin. Chem.* 2006, 52, 316-319.
(15) Wilson, W. J.; Erler, A. M.; Nasarabadi, S. L.; Skowronski, E. W.; Imbro, P. M. *Mol. Cell. Probes* 2005, 19, 137-144.
(16) Dunbar, S. A. *Clin. Chim. Acta* 2006, 363, 71-82.
(17) Yan, X. M.; Zhong, W. W.; Tang, A. J.; Schielke, E. G.; Hang, W.; Nolan, J. P. *Anal. Chem.* 2005, 77, 7673-7678.
(18) Hindson, B. J.; McBride, M. T.; Makarewicz, A. J.; Henderer, B. D.; Setlur, U.S.; Smith, S. M.; Gutierrez, D. M.; Metz, T. R.; Nasarabadi, S. L.; Venkateswaran, K. S.; Farrow, S. W.; Colston, B. W.; Dzenitis, J. M. *Anal. Chem.* 2005, 77, 284-289.
(19) Perkins, J.; Clavijo, A.; Hindson, B. J.; Lenhoff, R. J.; McBride, M. T. *Anal. Chem.* 2006, 78, 5462-5468.

What is claimed is:

1. A method of developing an assay for a target, comprising:
   providing an assay, comprising:
      a plurality of negative samples known to lack a target;
      a negative control signature that does not bind the target;
      a positive signature that binds the target;
      wherein each of the negative samples is combined with both the negative control signature and the positive signature;
   measuring one or more paired fluorescence intensities in each sample, wherein the fluorescence intensity pair consists of a fluorescence intensity of the negative control signature and a fluorescence intensity of the positive signature;
   determining, by linear regression, a correlation between the fluorescence intensities of the negative control signatures and the fluorescence intensities of the positive signatures;
   determining the distribution of orthogonal distances from the regression line to the points consisting of the paired fluorescence intensity measures; and
   choosing a threshold for the distance based on the distribution of orthogonal distances, wherein a distance between a measured fluorescence intensity pair and the regression line above the threshold the indicates a positive result in the assay, and a distance between a measured fluorescence intensity pair and the regression line below the threshold indicates a negative result in the assay.

2. The method of claim 1, wherein the threshold is chosen to give a desired false positive rate.

3. The method of claim 1, wherein the assay is a multiplexed array assay.

4. The method of claim 1, wherein the fluorescence intensity measurements are median fluorescence intensity (MFI) measurements.

5. A method of assaying a sample for a target, comprising:
   providing an assay, comprising:
      a plurality of negative samples known to lack a target;
      one or more samples to be assayed;
      a negative control signature that does not bind the target;
      a positive signature that binds the target;
      wherein each of the samples is combined with both the negative control signature and the positive signature;
   measuring one or more fluorescence intensities of each signature in each sample;
   determining, by linear regression, a correlation between the fluorescence intensities of the negative control signatures in the negative samples and the fluorescence intensities of the positive signatures in the negative samples;
   determining the orthogonal distance from the regression line to a point consisting of a measured fluorescence intensity of the negative control signature in an assayed sample, and the measured fluorescence intensity of the positive signature in the assayed sample; and
   determining whether or not the assayed sample contains the target based on the distance.

6. The method of claim 5, further comprising choosing a threshold value for the distance.

7. The method of claim 5, wherein the assay is a multiplexed array assay.

8. The method of claim 5, wherein the fluorescence intensity measurements are median fluorescence intensity (MFI) measurements.

* * * * *